(12) United States Patent
Jung et al.

(10) Patent No.: US 11,844,701 B2
(45) Date of Patent: Dec. 19, 2023

(54) GUIDER FOR SPINAL OPERATION AND CAGE THEREFOR

(71) Applicants: ENDOVISION CO., LTD., Daegu (KR); Min Ho Jung, Daegu (KR)

(72) Inventors: Min Ho Jung, Daegu (KR); Sae Won Eum, Seoul (KR)

(73) Assignees: Endovision Co., LTD.; Min Ho Jung

( * ) Notice: Subject to any disclaimer, the term of this patent is extended or adjusted under 35 U.S.C. 154(b) by 0 days.

(21) Appl. No.: 17/135,663

(22) Filed: Dec. 28, 2020

(65) Prior Publication Data

US 2022/0202585 A1    Jun. 30, 2022

(30) Foreign Application Priority Data

Dec. 24, 2020 (KR) .................. 10-2020-0183034

(51) Int. Cl.
*A61F 2/44* (2006.01)
*A61F 2/46* (2006.01)

(52) U.S. Cl.
CPC ............ *A61F 2/447* (2013.01); *A61F 2/4611* (2013.01); *A61F 2002/4629* (2013.01)

(58) Field of Classification Search
None
See application file for complete search history.

(56) References Cited

U.S. PATENT DOCUMENTS

| | | | | |
|---|---|---|---|---|
| 7,918,891 | B1* | 4/2011 | Curran | A61F 2/442 623/17.16 |
| 8,088,163 | B1* | 1/2012 | Kleiner | A61F 2/442 623/17.11 |
| 2004/0254428 | A1* | 12/2004 | Ritland | A61B 17/2812 600/220 |
| 2006/0063978 | A1* | 3/2006 | Ritland | A61B 17/02 600/213 |
| 2013/0103103 | A1* | 4/2013 | Mire | A61B 1/32 606/86 A |
| 2016/0213487 | A1* | 7/2016 | Wilson | A61F 2/44 |

* cited by examiner

*Primary Examiner* — Tessa M Matthews
(74) *Attorney, Agent, or Firm* — Mendelsohn Dunleavy, P.C.

(57) ABSTRACT

Proposed are a guider for a spinal operation and a cage therefor. The guider includes a sliding portion configured to guide a cage for a spinal operation and a holder to a surgical site, a head of the sliding portion being inserted into a human body region where a surgical incision is made for the spinal operation, and the cage for a spinal operation being combined with the holder; a support portion combined with one side of the sliding portion and thus supporting the sliding portion; and a handle combined with the support portion.

11 Claims, 8 Drawing Sheets

GUIDER FOR SPINAL OPERATION AND CAGE THEREFOR

The national research and development project supporting the present disclosure is as follows:
Project Serial Number: 1415166420
Project Number: P0006714
Government Ministry: Ministry of Trade, Industry and Energy
Research Management Specialized Institution: Korea Institute for Advancement of Technology
Research Project Name: National innovation cluster project
Research Topic: Development of a solution for 3D image reconstruction, intelligent and customized operation planning and post-operation care using biosignals
Contribution Ratio: 100
Managing Institution: Endovision Co., Ltd.
Research Period: Oct. 1, 2018 to Dec. 31, 2020

CROSS REFERENCE TO RELATED APPLICATION

The present application claims priority to Korean Patent Application No. 10-2020-0183034, filed Dec. 24, 2020, the entire contents of which is incorporated herein for all purposes by this reference.

BACKGROUND OF THE INVENTION

Field of the Invention

The present disclosure relates to a guider for a spinal operation and a cage therefor and, more particularly, to a guider for a spinal operation, which is inserted into a human body region where a surgical incision is made for the spinal operation and guides a holder with which a cage for the spinal operation is combined to a surgical site, and a wide-type cage that is guided by the guider for the spinal operation.

Description of the Related Art

Always, the spine is normally made up of 24 bones (except a sacra). Joints connect the bones to each other. A disc is positioned between the joints. Each disc absorbs shock occurring whenever the human body moves or the joints function and support the resulting load.

The spine with this configuration serves to cushion the shock and to support a human body's posture. Furthermore, the spine stabilizes the body in the upright position and provides support for the thorax and the abdomen.

However, when the spine is damaged or misaligned due to an external artificial factor, degenerative arthritis, or a persistent abnormal posture, nerves passing through vertebral canals are pressed, thereby causing great pain.

That is, a patient who has a damaged spine cannot lead a normal life. Even if the degree of damage is not severe, the damaged region of the spine is pressed against adjacent internal organs, thereby causing pain.

A cage is an interbody fusion device that is used in spinal fusion which is one of orthopedic surgical techniques. Such a cage is a type of implant that is placed between vertebrae after removing a damaged disc, to graft a lumbar vertebra or to treat spine misalignment and deviation.

A cage in the related art has a smaller size than a surgical site, and thus causes a subsidence phenomenon. The cage in the related art has the disadvantage of having a low fusion rate.

In addition, when performing a spinal operation, the cage in the related art is caused to approach anterior vertebrae in front of which there are many major blood vessels. Thus, approaching the anterior vertebrae increases the burden of performing the spinal operation. The cage, which is caused to approach the anterior vertebrae, is placed between vertebrae using a holder and is rotated to adjust a position and direction thereof.

During a process of inserting the cage, an injury may be caused to tissue of a surgically incised region. Furthermore, possible transformation of a shape of the tissue of the surgically incised region during the spinal operation may make it difficult to perform the spinal operation.

Moreover, the insertion of the cage anterior to the vertebrae and the insertion of a spine alignment crew posterior to the vertebrae make it difficult to perform the spinal operation. Thus, it has been known that only experienced surgeons can successfully perform such a spinal operation.

The foregoing is intended merely to aid in the understanding of the background of the present disclosure and is not intended to mean that the present disclosure falls within the purview of the related art that is already known to those skilled in the art.

SUMMARY OF THE INVENTION

An objective of the present disclosure is to provide a guider for a spinal operation, which is capable of being inserted into a human body region where a surgical incision is made for the spinal operation and guiding a holder with which a cage for the spinal operation is combined to a surgical site, and a wide-type cage that is capable of being guided by the guider for the spinal operation.

According to an aspect of the present disclosure, there is provided a guider for the spinal operation, the guider including: a sliding portion configured to guide a cage for a spinal operation and a holder to a surgical site, a head of the sliding portion being inserted into a human body region where a surgical incision is made for the spinal operation, and the cage for a spinal operation being combined with the holder; a support portion combined with one side of the sliding portion and thus supporting the sliding portion; and a handle combined with the support portion.

In the guider, the sliding portion may include a first slider and a second slider, which are spaced apart from each other in such a manner as to face each other to secure a space, and the holder with which the cage is combined may be inserted into the space.

In the guider, the head may extend while being bent at a predetermined angle inward from front ends of the first slider and the second slider in such a manner as to face each other so that the space is narrowed.

In the guider, the sliding portion may include upper guides extending while being bent at a predetermined angle inward from tops, respectively, of the first slider and the second slider so that the space is narrowed.

In the guider, the sliding portion may include lower guides extending while being bent at a predetermined angle inward from bottoms, respectively, of the first slider and the second slider so that the space is narrowed.

In the guider, the support portion may be Y-shaped, and upper end portions of the Y-shaped support portion may be combined with rear end portions, respectively, of the first slide and the second slider.

In the guider, the Y-shaped support portion may be separated into two parts, one for supporting the first slider and the other for supporting the second slider.

The Y-shaped support portion may surround the rear end portions of the first slider and the second slider and may have an elastic part formed in one side thereof.

According to another aspect of the present disclosure, there is provided a cage for a spinal operation, the cage being guided by the above-described guider for the spinal operation. The cage includes: a main body having streamlined front and rear portions; directional protrusions formed on upper and lower surfaces of the main body; and a combination portion formed on a rear end of the main body, with the holder being combined with the combination portion.

In the cage, the main body may have one mesh-shaped side surface.

In the cage, the main body may have a window that is formed through the main body vertically, horizontally, or vertically and horizontally.

In the cage, the window may be divided by a partition wall into a plurality of windows.

In the cage, the combination portion may include: a threaded hole into which the holder is screwed; and combination holes formed on left and right sides, respectively, of the threaded hole.

In the cage, a length of the main body in a width direction may be 0.5 to 1 times a length of the main body in a lengthwise direction.

In the cage, the cage may be caused to approach posterior vertebrae and may be placed between vertebrae and the cage may be made of a titanium or PEEK material.

The guider for the spinal operation according to the present disclosure inserted into the human body region where the surgical incision is made for the spinal operation, and guides the holder with which the cage for the spinal operation is combined to the surgical site. During a process of inserting the cage when performing the spinal operation, the guider for the spinal operation can prevent an injury to tissue of the human body region where the surgical incision is made. Thus, the guider has the advantage of facilitating the spinal operation.

In addition, the cage that is guided by the guider for the spinal operation according to the present disclosure is formed as a wide-type cage adjusted fittingly for the surgical site. The cage can prevent side effects due to a subsidence phenomenon. Thus, the cage has the advantage of having a high fusion rate.

In addition, the cage according to the present disclosure is caused to approach posterior vertebrae when performing the spinal operation. There are many major blood vessels in front of the cage that moves toward anterior vertebrae. Thus, approaching the posterior vertebrae provides a smaller burden of performing the spinal operation than approaching the anterior vertebrae. When caused to approach the posterior vertebrae, the cage is placed by the holder between vertebrae, and then is rotated to easily adjust a position and direction thereof.

In addition, the cage according to the present disclosure is inserted posterior to the vertebrae, and a screw for spinal alignment is also inserted posterior to the vertebrae. Thus, the cage has the advantage of facilitating the spinal operation.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

The present disclosure relates to a guider for a spinal operation that is inserted into a human body region where a surgical incision is made for the spinal operation, and guides a holder with which a cage for a spinal operation is combined to a surgical site. During a process of inserting the cage when performing the spinal operation, the guider for the spinal operation serves to prevent an injury to tissue of the human body region where the surgical incision is made. Thus, the guider facilitates the spinal operation.

In addition, the cage that is guided by the guider for the spinal operation according to the present disclosure is formed as a wide-type cage adjusted fittingly for the surgical site. The cage can prevent side effects due to a subsidence phenomenon. Thus, the cage has the advantage of having a high fusion rate.

In addition, the cage according to the present disclosure is caused to approach posterior vertebrae when performing the spinal operation. However, there are many major blood vessels in front of the cage that moves toward anterior vertebrae. Thus, approaching the posterior vertebrae provides a smaller burden of performing the spinal operation than approaching the anterior vertebrae. When caused to approach the posterior vertebrae, the cage is placed by the holder between vertebrae, and then is rotated to easily adjust a position and direction thereof.

In addition, the cage according to the present disclosure is inserted posterior to the vertebrae, and a screw for spinal alignment is also inserted posterior to the vertebrae. Thus, the cage has the advantage of facilitating the spinal operation.

Figure 1:
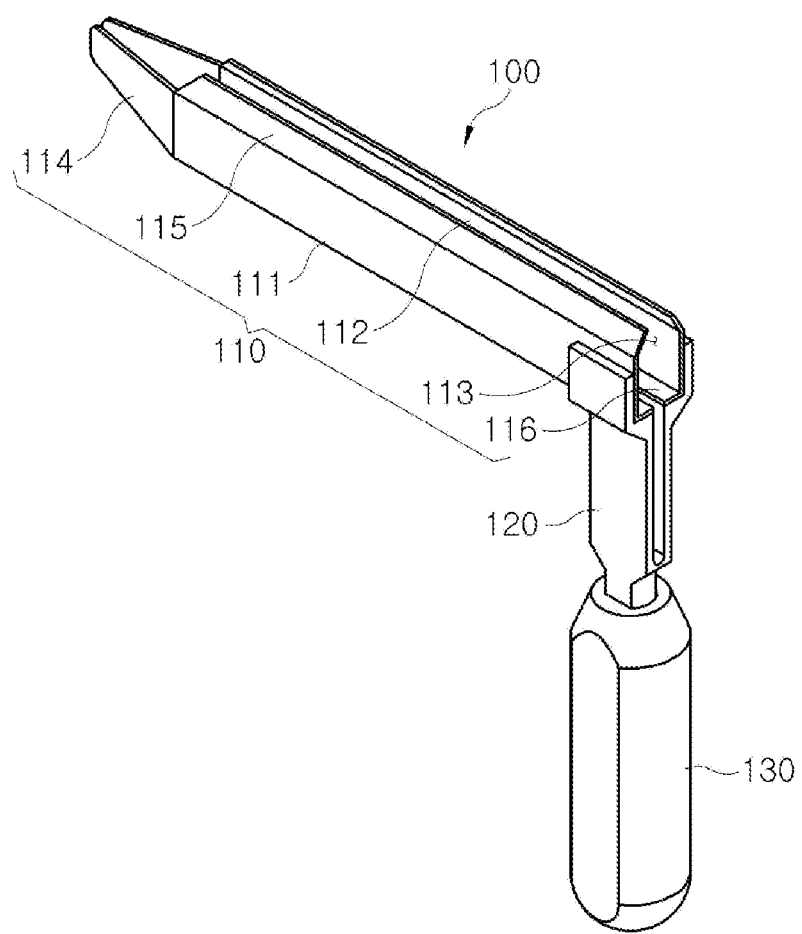
FIG. 1 is a perspective view illustrating a guider for a spinal operation according to an embodiment of the present disclosure.
Figure 2:
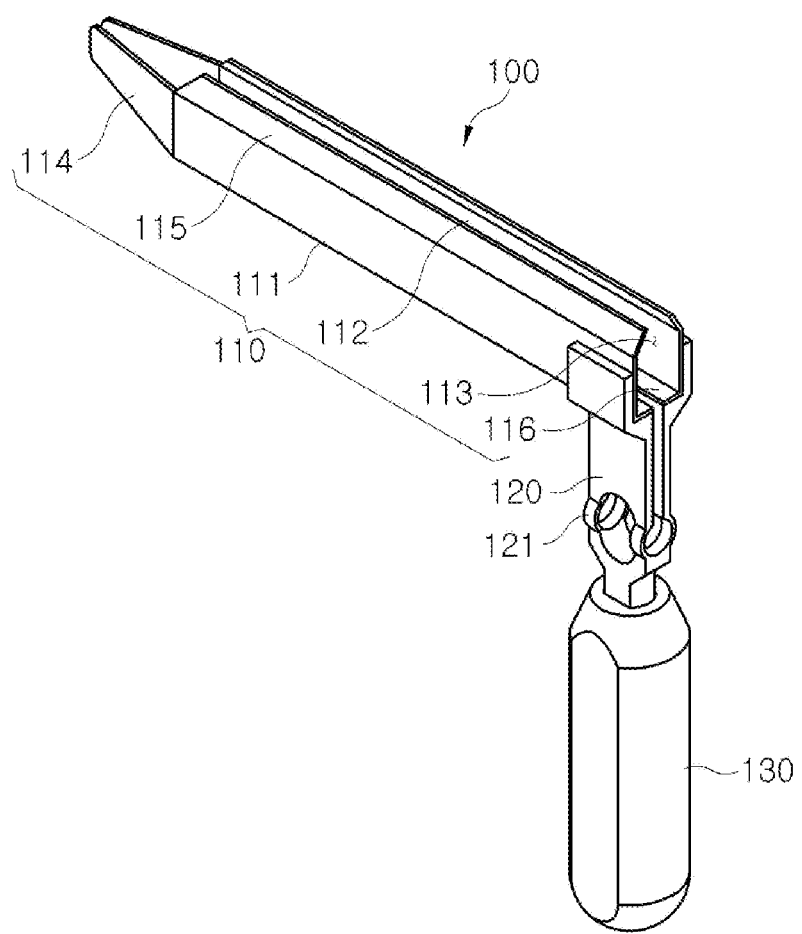
FIG. 2 is a perspective view illustrating a guider for a spinal operation according to another embodiment of the present disclosure.
Figure 3:
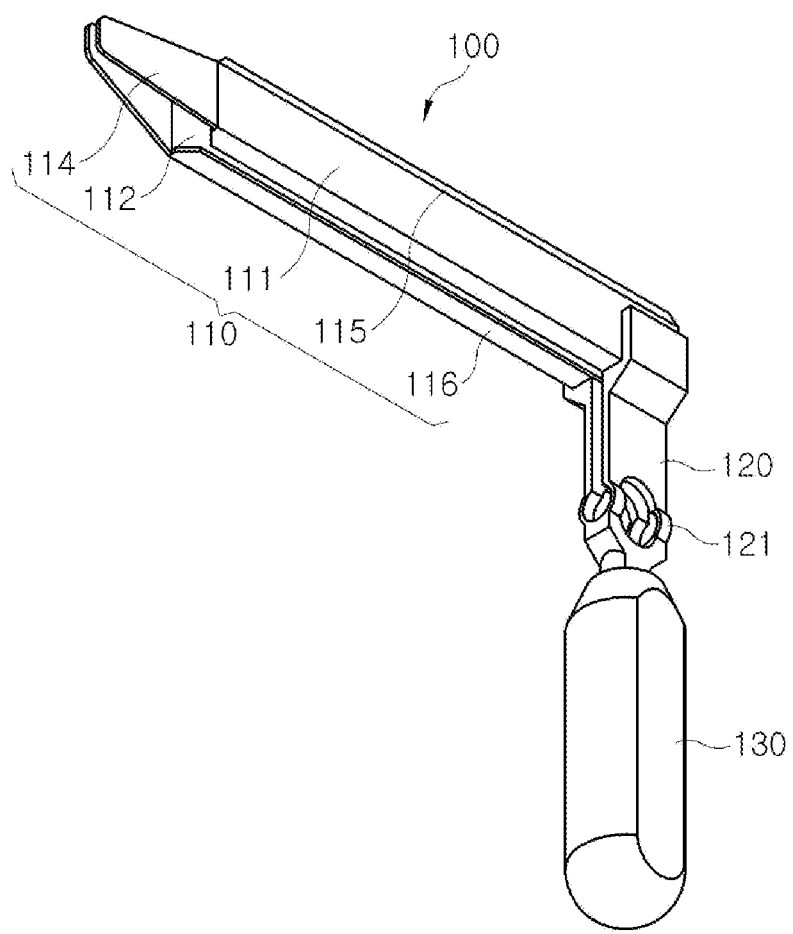
FIG. 3 is a perspective view illustrating a bottom surface of the guider for the spinal operation according to the embodiment of the present disclosure.
Figure 4:
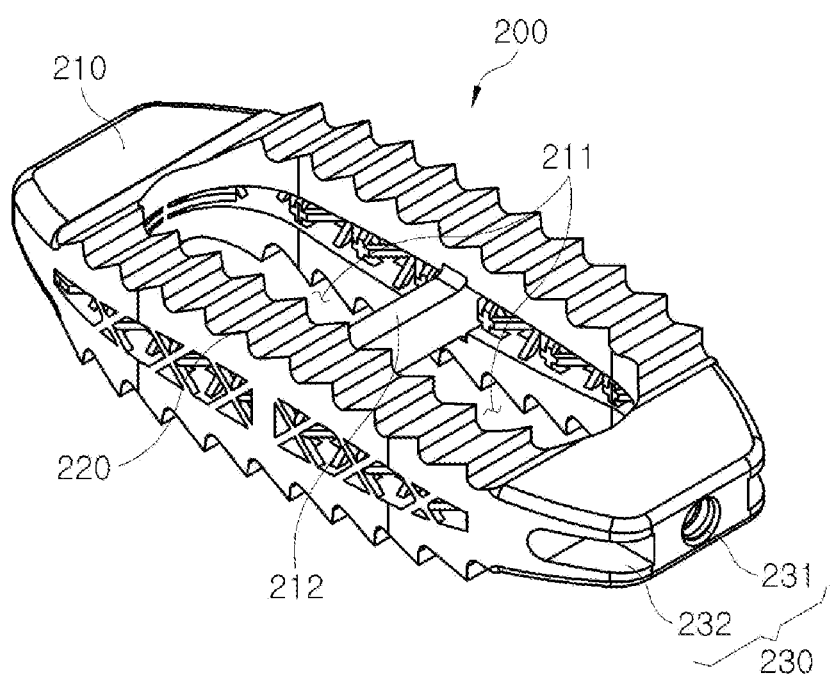
FIG. 4 is a perspective view illustrating a cage according to an embodiment of the present disclosure.
Figure 5A:
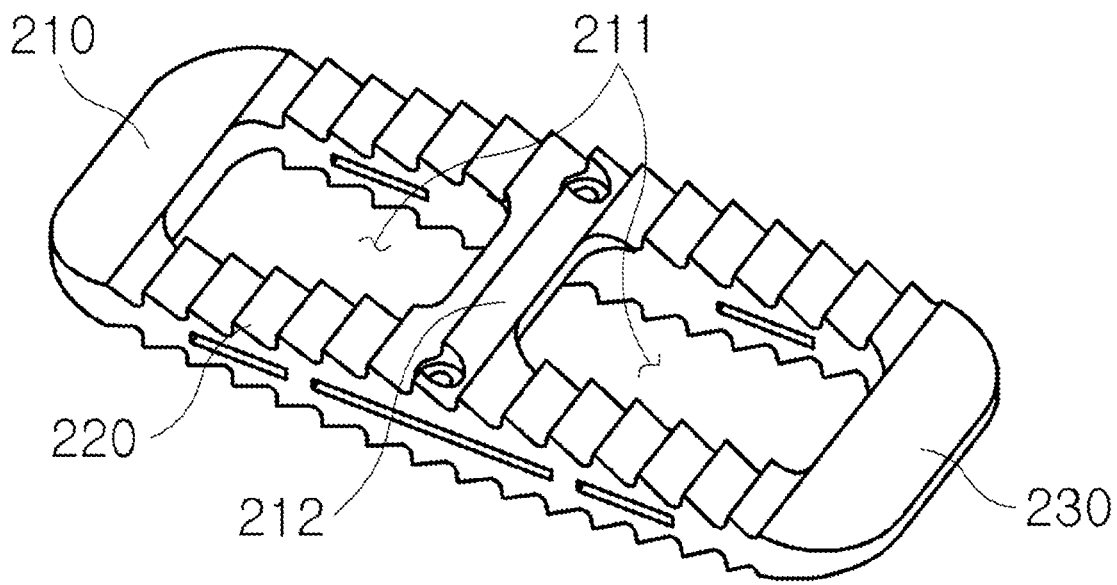
FIGS. 5A to 5C are perspective views illustrating a cage according to another embodiment of the present disclosure.
Figure 5B:
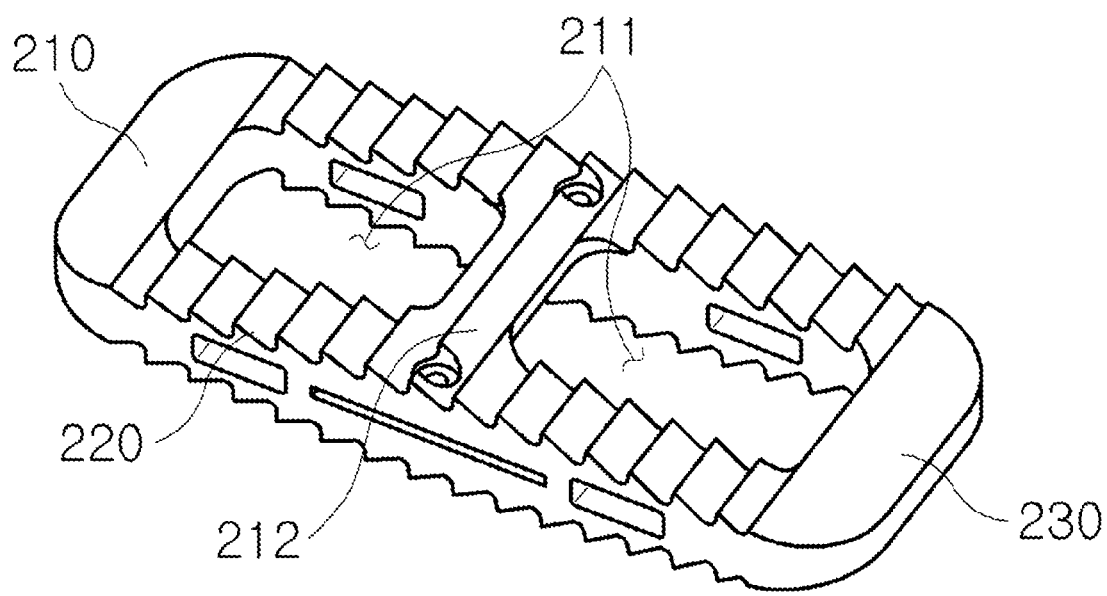
Figure 5C:
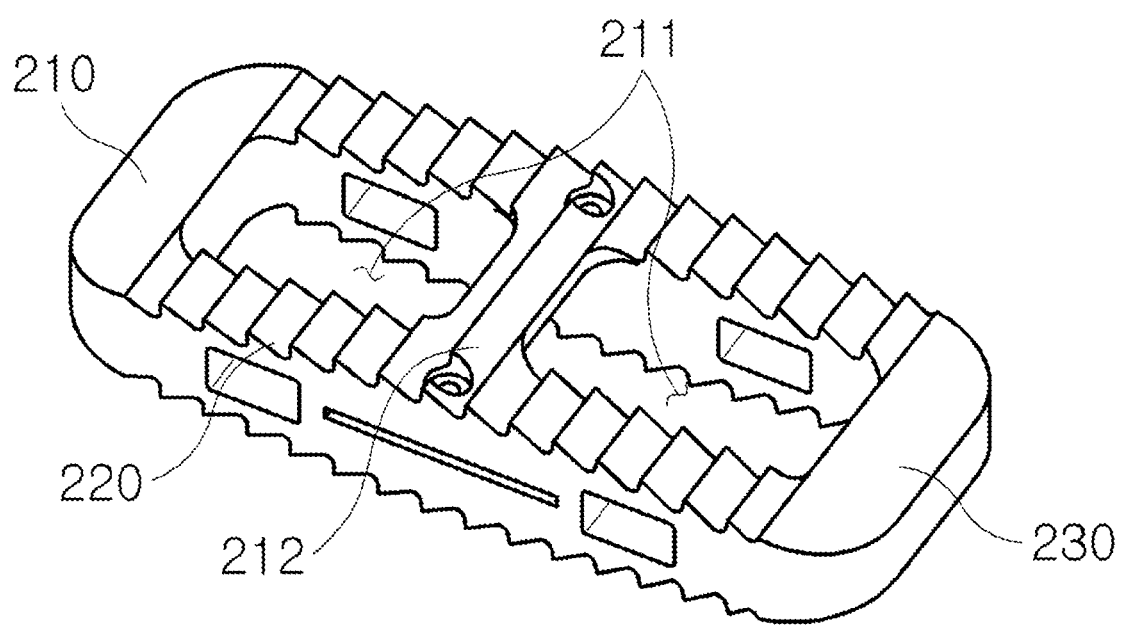
Figure 6:
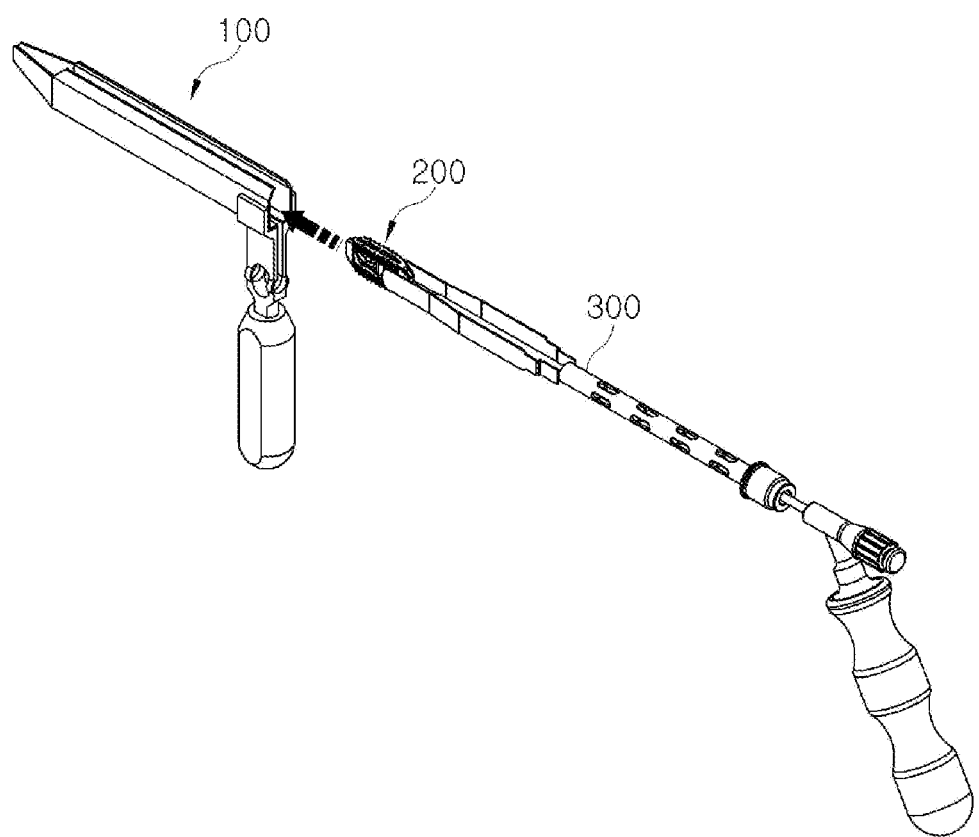
FIG. 6 is a schematic view illustrating a state where a holder with which the cage is combined is inserted into the guider for the spinal operation according to the embodiment of the present disclosure.
Figure 7:
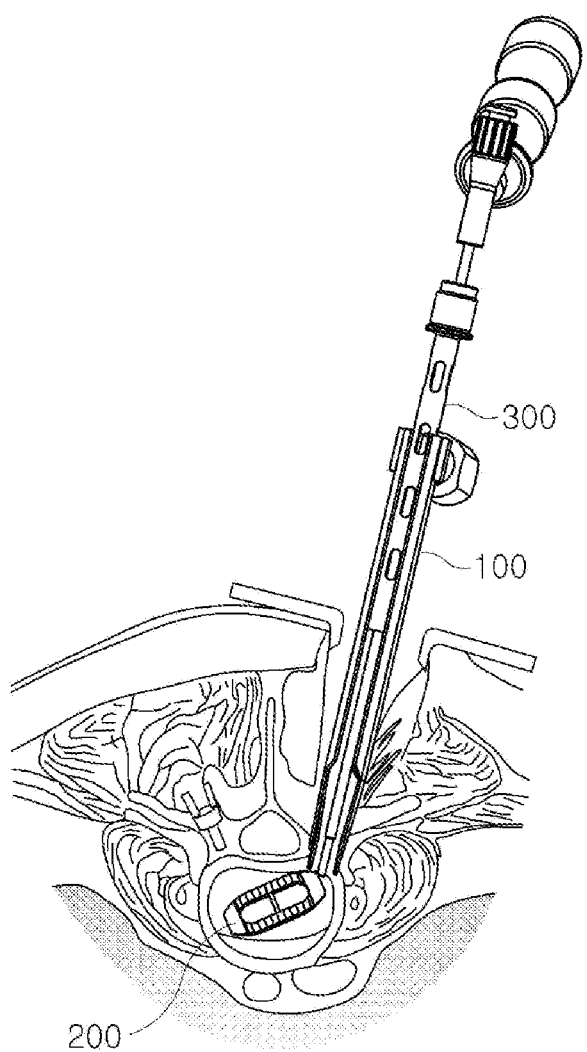
FIG. 7 is a schematic view illustrating a spinal operation situation where the holder with which the cage is combined is guided by the guider for the spinal operation according to the embodiment of the present disclosure.

Embodiments of the present disclosure will be described below with reference to the accompanying drawings. FIG. 1 is a perspective view illustrating a guider for a spinal operation according to an embodiment of the present disclosure. FIG. 2 is a perspective view illustrating a guider for a spinal operation according to another embodiment of the present disclosure. FIG. 3 is a perspective view illustrating a bottom surface of the guider for the spinal operation according to the embodiment of the present disclosure. FIG. 4 is a perspective view illustrating a cage according to an embodiment of the present disclosure. FIGS. 5A to 5C are perspective views illustrating a cage according to another embodiment of the present disclosure. FIG. 6 is a schematic view illustrating a state where a holder with which the cage is combined is inserted by the guider for the spinal operation according to the embodiment of the present disclosure. FIG. 7 is a schematic view illustrating a spinal operation situation where the holder with which the cage is combined is guided by the guider for the spinal operation according to the embodiment of the present disclosure.

As illustrated, the guider 100 for the spinal operation according to the present disclosure includes a sliding portion 110, a support portion 120, and a handle 130. A head 114 of the sliding portion 110 is inserted into the human body region where the surgical incision is made for the spinal operation. A holder 300 with which a cage 200 for the spinal operation is combined is inserted into the sliding portion 110. In this manner, the sliding portion 110 guides the cage 200 and the holder 300 to the surgical site. The support portion 120 is combined with one side of the sliding portion 110 and supports the sliding portion 110. The handle 130 is combined with the support portion 120.

The guider 100 for the spinal operation according to the present disclosure is inserted into the human body region where the surgical incision is made for the spinal operation, and guides the holder 300 with which the cage 200 for the spinal operation is combined to the surgical site. The guider 100 prevents the injury to the tissue of the surgically incised region during the process of inserting the cage 200 and facilitates the spinal operation.

The guider 100 for the spinal operation according to the present disclosure includes the sliding portion 110 as a principal constituent element. The head 114 of the sliding portion 110 is inserted into the human body region where the surgical incision is made for the spinal operation. The holder 300 with which the cage 200 for the spinal operation is combined is inserted into the sliding portion 110. In this manner, the sliding portion 110 guides the cage 200 and the holder 300 to the surgical site.

When the head 114 is inserted into the surgically incised region and thus the cage 200 and the holder 300 are inserted into the surgically incised region, the sliding portion 110 serves to protect the tissue of the surgically incised region from injury. Particularly, the sliding portion 110 finds useful application in a wide-type cage 200.

The sliding portion 110 is formed to such a length that the head 114 is inserted into the surgically incised region and thus the cage 200 and the holder 300 are stably guided to the surgical site. To facilitate the insertion of the head 114 into the surgically incised region, the more a front end of the head 114 is approached, the smaller the width of the header 114.

Since the cage 200 and the holder 300 are guided to be inserted into the sliding portion 110, the sliding portion 110 is formed to have a space 113 sufficient to permit the cage 200 and the holder 300 to move therein.

In addition, it is preferable that the sliding portion 110 is formed to have elasticity in such a manner that the space 113 varies flexibly in size according to a shape of the surgical site to which the cage 200 and the holder 300 are guided by the sliding portion 110, a shape of the surgically incised region, and shapes of the cage 200 and the holder 300.

That is, the sliding portion 110 according to an embodiment of the present disclosure is formed to a predetermined length. Furthermore, the sliding portion 110 is formed to have the space 113 inside in such a manner that the cage 200 and the holder 300 moves therein. More specifically, the sliding portion 110 is formed to have a structure in which a front portion thereof has a narrow width to facilitate the insertion into the surgically incised region and in which the cage 200 and the holder 300 are inserted into the sliding portion 110 through a rear end thereof.

The sliding portion 110 as a whole may be formed as one piece in such a manner as to guide the cage 200 and the holder 300. As described above, preferably, the sliding portion 110 is formed in such a manner that the space 113 changes flexibly in size when the sliding portion 110 is elastically transformed with a predetermined force.

Specifically, as illustrated in FIGS. 1 to 3, a first slider 111 and a second slider 112 are separately formed to be spaced apart from each other in such a manner as to face each other so that the space 113 is provided. The holder 300 with which the cage 200 is combined is inserted through the space 113.

As described above, the sliding portion 110 includes the head 114 is inserted into the human body region where the surgical incision is made for the spinal operation. The head 114 extends while being bent at a predetermined angle inward from front ends of the first slider 111 and the second slider 112 so that the space 113 is narrowed. Thus, the insertion of the head 114 into the surgically incised region is facilitated.

In addition, the guider 100 for the spinal operation according to the present disclosure includes upper guides 115. The upper guides 115 are formed on the tops, respectively, of the first slider 111 and the second slider 112 in such a manner as to extend while being bent at a predetermined angle inward from the tops of the first slider 111 and the second slider 112 so that the space 113 is narrowed.

In addition, the guider 100 for the spinal operation includes lower guides 116. The lower guides 116 are formed on the bottoms, respectively, of the first slider 111 and the second slider 112 in such a manner as to extend while being bent at a predetermined angle inward from the bottoms of the first slider 111 and the second slider 112 so that the space 113 is narrowed.

The upper guides 115 and the lower guides 116 are formed to prevent the inserted cage 200 and holder 300, which are inserted into the space 113, from deviating from the space 113. Since the first slider 111 and the second slider 112 are separably formed, the upper guides 115 and the lower guides 116 are also separately formed.

The upper guides 115 are positioned a predetermined distance away from each other in such a manner as to face each other at the predetermined angle. The lower guides 116 are also positioned a predetermined distance away from each other in such a manner as to face each other at the predetermined angle. Thus, the space 113 has room for the flexible change in size when the sliding portion 110 is elastically transformed.

The support portion 120 is combined with one side of the sliding portion 110 and thus supports the sliding portion 110. The support portion 120 is formed to make a predetermined angle with respect to the sliding portion 110 to prevent interference therewith.

According to an embodiment of the present disclosure, the support portion 120 is Y-shaped. Upper end portions of the Y-shaped support portion 120 are combined with rear end portions, respectively, of the first slide 111 and the second slider 112.

In addition, the Y-shaped support portion 120 is separated into two parts, one for supporting the first slider 111 and the other for supporting the second slider 112.

That is, according to the present disclosure, preferably, the sliding portion 110 has separated left and right sliders and the support portion 120 has separated left and right upper end parts and separated left and right middle parts. The reason for this is that, as described above, with the elastic force of the sliding portion 110, the space 113 needs to vary flexibly in size according to the shape of the surgical site to which the cage 200 and the holder 300 are guided by the sliding portion 11, the shape of the surgically incised region, and the shapes of the cage 200 and the holder 300.

In addition, the support portion 120 is formed to surround the rear end portions of the first slider 111 and the second slider 112, thereby maintaining a state where the support portion 120 are stably combined with the first slider 111 and the second slider 112. Thus, the elastic force of the sliding portion is more widely distributed.

In addition, as illustrated in FIGS. 2 and 3, an elastic part 121 may be formed in one side of the support portion 120 in order for the space 113 to change flexibly in size.

The handle 130 is combined with the support portion 120 in order of a user to conveniently use the guider for the spinal operation.

The handle 130 is combined with a lower end portion of the support portion 120 by means of screwing, welding, or the like. The handle 130 is combined with the support portion 120 in such a manner to have the same centerline as the support portion 120.

The handle 130 as a whole has a cylinder-like shape and may have a circumferential surface in a polyhedral shape. The circumferential surface may be corrugated. Directions may be marked on the circumferential surface.

The guider for the spinal operation according to the present disclosure, which has the configuration described above, is inserted into the human body region where the surgical incision is made for the spinal operation and guides the holder with which the cage for the spinal operation is combined to the surgical site. Thus, when performing the spinal operation, the guider for the spinal operation prevents the injury to the tissue of the surgically incised region in the process of inserting the cage and facilitates the spinal operation.

The cage 200 for the spinal operation according to the present disclosure is guided by the guider 100 for the spinal operation.

The cage 200 according to an embodiment of the present disclosure includes a main body 210, directional protrusions 220, and a combination portion 230. The main body 210 has front and rear portions formed in a streamlined manner. The directional protrusions 220 are formed on upper and lower surfaces of the main body 210. The holder 300 is combined with the combination portion 230 that is formed on a rear end of the main body 210.

In addition, it is preferable that the cage 200 to be guided by the guider 100 for the spinal operation according to the present disclosure is formed as a wide-type cage adjusted fittingly for the surgical site. The wide-type cage prevents the side effects due to the subsidence phenomenon and has the advantage of having a high fusion rate.

The wide-type cage according to the present disclosure is a cage in which the length of the main body 210 in a width direction is 0.5 to 1 times the length of the main body 210 in a lengthwise direction.

In addition, the cage 200 according to the present disclosure the cage 200 is made of a titanium or PEEK material, which has a strong affinity for the human body and a high fusion rate.

The main body 210 has the front and rear portions formed in a streamlined manner. Thus, the main body 210 prevents injury to nerves or muscle tissue when inserting the cage 200, which is an interbody fusion cage. Furthermore, the main body 210 has the advantages of facilitating the insertion of the cage 200 and conveniently changing a direction of the cage 200.

In addition, the main body 210 may have a window 211 that is formed through the main body 210 vertically, horizontally, or vertically and horizontally.

The window 211 is filled with a bone chip, such as an artificial bone or an autogenous bone, or bone cement, and serves to increase a rate of fusion with a bone grown from an adjacent vertebra.

A single window 211 or a plurality of windows 211 may be formed, considering a shape of a vertebra, a fusion rate depending on a lesion, and the like. The plurality of windows may be formed by dividing the window 211 by a partition wall 212.

In addition, one side surface of the main body 210 may be formed in the shape of a mesh. The mesh-shaped main body 210 contributes to stably placing the cage 200 between the vertebrae and to rapid tissue regeneration, thereby increasing the fusion rate.

FIG. 4 illustrates that one side surface of the main body 210 is formed in the shape of a mesh and that the window 211 is vertically formed. FIGS. 5A to 5C illustrate that the windows 211 are vertically formed on the left and right sides, respectively, of the main body 210. The main body 210 and the window 211 are designed in terms of shape and number, considering the shape of the vertebra, the fusion rate depending on a lesion, and the like.

It is preferable that the directional protrusions 220 are formed on upper and lower surfaces of the main body 210. The reason for this is to stably place the cage 200 between the vertebrae and thus increase the fusion rate.

Particularly, surfaces (front surfaces), in the direction of the surgical site, of the directional protrusions 220 are formed at a low angle, and surfaces (rear surfaces), in the opposite direction, of the directional protrusions 220 are formed at an angle higher than the angle at which the front surfaces are formed. The reason for this is to facilitate the spinal operation and prevent the cage 200 from moving freely between the vertebrae.

The holder 300 is combined with the combination portion 230, formed on the rear end of the main body 210. The combination portion 230 includes a threaded hole 231 and combination holes 232. For combination, the holder 300 is screwed into the threaded hole 231. For stable combination, the combination holes 232 are formed at the right and left sides, respectively, of the threaded hole 231.

The combination holes 232 may be formed according to a lesion situation or the surgical site. The combination of the cage 200 with the holder 300 or a separated instrument through the combination holes 232 facilitates the insertion of the cage 200 and the positioning thereof.

FIG. 6 illustrates a state where the holder 300 with which the cage 200 is combined is inserted into the guider 100 for the spinal operation according to the embodiment of the present disclosure. FIG. 7 illustrates a spinal operation situation where the holder 300 with which the cage 200 is combined is guided by the guider 100 for the spinal operation according to the embodiment of the present disclosure.

The guider 100 for the spinal operation according to the present disclosure minimizes injuries to nerves and muscles adjacent to the surgically incised region, and makes possible the stable placing of the cage 200 between the vertebrae, thereby facilitating the spinal operation.

Along with the holder 300, the cage 200 according to the present disclosure is guided by the guider for the spinal operation and thus is placed between the vertebrae without causing the injury to the tissue adjacent to the surgically incised region.

In addition, the cage 200 is formed as a wide-type cage adjusted fittingly for the surgical site. Thus, the cage 200 prevents the side effects due to the subsidence phenomenon and has the advantage of having a high fusion rate.

In addition, the cage according to the present disclosure is caused to approach posterior vertebrae when performing the spinal operation. However, there are many major blood vessels in front of the cage that moves toward anterior vertebrae. Thus, approaching the posterior vertebrae provides a smaller burden of performing the spinal operation than approaching the anterior vertebrae. When caused to approach the posterior vertebrae, the cage is placed by the holder between vertebrae, and then is rotated to easily adjust a position and direction thereof.

In addition, the cage according to the present disclosure is inserted posterior to the vertebrae, and a screw for spinal alignment is also inserted posterior to the vertebrae. Thus, the cage has the advantage of facilitating the spinal operation.

Although the specific embodiment of the present disclosure has been described for illustrative purposes, those skilled in the art will appreciate that various modifications, additions, and substitutions are possible, without departing from the scope and spirit of the disclosure as disclosed in the accompanying claims.

What is claimed is:

1. A guider for a spinal operation, the guider comprising:
    a sliding portion configured to guide a cage for a spinal operation and a holder to a surgical site, wherein the sliding portion having a predetermined length comprises a first slider and a second slider, which are separated, parallel and spaced apart from each other in such a manner as to face each other to secure a space,
    a head of the sliding portion being configured for insertion into a human body region where a surgical incision is made for the spinal operation, and to guide the cage for the spinal operation when combined with the holder, wherein the head of the sliding portion extends while being bent at a predetermined angle inward from front ends of the first slider and the second slider in such a manner as to face each other so that the space approaching a front end of the head of the sliding portion narrows in a V-shaped manner, and the front end of the head of the sliding portion is along a same axis as the predetermined length of the sliding portion;
    a support portion combined with one side of the sliding portion and thus supporting the sliding portion, wherein the support portion is at a predetermined angle that is not horizontal with the sliding portion to prevent interference with guiding the cage and the holder to the surgical site by the sliding portion; and
    a handle having a cylinder-like shape combined with the support portion in such a manner as to have a same centerline as the support portion.

2. The guider of claim 1, wherein the sliding portion comprises:
    upper guides extending while being bent at a predetermined angle inward from tops, respectively, of the first slider and the second slider so that the space is narrowed.

3. The guider of claim 1, wherein the sliding portion comprises:
    lower guides extending while being bent at a predetermined angle inward from bottoms, respectively, of the first slider and the second slider so that the space is narrowed.

4. The guider of claim 1, wherein the support portion is Y-shaped, and
    upper end portions of the Y-shaped support portion are combined with rear end portions, respectively, of the first slide and the second slider.

5. The guider of claim 4, wherein the Y-shaped support portion is separated into two parts, one for supporting the first slider and the other for supporting the second slider.

6. The guider of claim 4, wherein the Y-shaped support portion is configured to surround the rear end portions of the first slider and the second slider.

7. The guider of claim 4, wherein the Y-shaped support portion has an elastic part formed in one side thereof.

8. A system for a spinal operation, comprising the guider of claim 1, and a cage comprising:
    a main body having streamlined front and rear portions, wherein:
    the main body has a window that is formed through the main body vertically, horizontally, or vertically and horizontally,
    the window is divided by a partition wall into a plurality of windows, and
    a length of the main body in a width direction is 0.5 to 1 times a length of the main body in a lengthwise direction.

9. The system of claim 8, wherein the main body has one mesh-shaped side surface.

10. The system of claim 8, further comprising a combination portion formed on a rear end of the main body, configured for combination with a holder, wherein the combination portion comprises:
    a threaded hole into which the holder is screwed; and
    combination holes formed on left and right sides, respectively, of the threaded hole.

11. The system of claim 8, wherein the cage is made of a titanium or PEEK material.

* * * * *